US011241539B2

(12) United States Patent
Folk et al.

(10) Patent No.: US 11,241,539 B2
(45) Date of Patent: Feb. 8, 2022

(54) AUTOINJECTOR WITH LOW ENERGY PLUNGER LOADING

(71) Applicant: AMGEN INC., Thousand Oaks, CA (US)

(72) Inventors: Christopher R. Folk, Los Angeles, CA (US); Scott R. Gibson, Granada Hills, CA (US); Brian J. Intoccia, Denver, CO (US)

(73) Assignee: AMGEN INC., Thousand Oaks, CA (US)

( * ) Notice: Subject to any disclaimer, the term of this patent is extended or adjusted under 35 U.S.C. 154(b) by 835 days.

(21) Appl. No.: 15/307,501

(22) PCT Filed: Jun. 26, 2015

(86) PCT No.: PCT/US2015/038049
§ 371 (c)(1),
(2) Date: Oct. 28, 2016

(87) PCT Pub. No.: WO2016/003813
PCT Pub. Date: Jan. 7, 2016

(65) Prior Publication Data
US 2017/0106146 A1 Apr. 20, 2017

Related U.S. Application Data

(60) Provisional application No. 62/019,729, filed on Jul. 1, 2014.

(51) Int. Cl.
*A61M 5/20* (2006.01)
*A61M 5/315* (2006.01)
(Continued)

(52) U.S. Cl.
CPC .......... *A61M 5/20* (2013.01); *A61M 5/31571* (2013.01); *A61M 5/31576* (2013.01);
(Continued)

(58) Field of Classification Search
CPC .. A61M 5/20; A61M 5/2033; A61M 5/31571; A61M 5/3243; A61M 5/3245;
(Continued)

(56) References Cited

U.S. PATENT DOCUMENTS 3,797,489 A * 3/1974 Sarnoff ............... A61M 5/2033
604/136
6,210,369 B1 * 4/2001 Wilmot ............... A61M 5/2033
604/157
(Continued)

FOREIGN PATENT DOCUMENTS

| JP | 2013-520214 A | 6/2013 | |
| WO | WO-0024441 A1 | 5/2000 | |
| WO | WO-03097133 A1 * | 11/2003 | .......... A61M 5/2033 |

OTHER PUBLICATIONS

Japanese Patent Application No. 2016-572232, Office Action, dated May 14, 2019.
(Continued)

*Primary Examiner* — James D Ponton
(74) *Attorney, Agent, or Firm* — Marshall, Gerstein & Borun LLP

(57) ABSTRACT

An injection device, method, and system for drug delivery includes a container for storing a drug, the container having a stopper movably disposed in the container for expelling the drug; an injection drive mechanism having a plunger for acting on the stopper and an energy source having a first selected potential energy for exerting a force on the plunger to cause the plunger to act on the stopper to expel the drug; and a plunger loading mechanism for substantially preventing the plunger from accelerating to a predetermined velocity before it acts on the stopper. The plunger loading mechanism may be a spring having a second selected potential energy for reducing or eliminating a distance between the plunger and the stopper, prior to the plunger (Continued)

accelerating to the velocity. The second selected potential energy of the spring may be less than the first selected potential energy of the energy source.

11 Claims, 14 Drawing Sheets

(51) Int. Cl.
*A61M 5/32* (2006.01)
*A61M 5/31* (2006.01)

(52) U.S. Cl.
CPC ... *A61M 5/3245* (2013.01); *A61M 2005/2013* (2013.01); *A61M 2005/3143* (2013.01)

(58) Field of Classification Search
CPC .......... A61M 5/326; A61M 2005/2013; A61M 2005/206; A61M 2005/208; A61M 2005/2086; A61M 2005/3143; A61M 2005/3247; A61M 2005/3267; A61M 2005/3268; A61M 5/31576; A61M 2005/3142
See application file for complete search history.

(56) References Cited

U.S. PATENT DOCUMENTS

| | | | |
|---|---|---|---|
| 2010/0094214 A1* | 4/2010 | Abry | A61M 5/2033 604/110 |
| 2013/0204195 A1 | 8/2013 | Ekman et al. | |
| 2013/0237921 A1 | 9/2013 | Lannan et al. | |
| 2013/0274666 A1* | 10/2013 | Brereton | A61M 5/2033 604/117 |
| 2013/0317447 A1* | 11/2013 | Cowe | A61M 5/2033 604/196 |
| 2016/0106920 A1* | 4/2016 | Stefansen | A61M 5/2033 604/198 |

OTHER PUBLICATIONS

International Search Report for PCT/US2015/038049, dated Jul. 10, 2015.
International Preliminary Report on Patentability and Written Opinion of the International Searching Authority for International Application No. PCT/US2015/038049, dated Jan. 3, 2017.
Australian Patent Application No. 2015284463, Examination Report No. 1, dated Feb. 27, 2019.
Mexican Patent Application No. MX/a/2016/016900, Office Action, dated Jan. 22, 2020.

* cited by examiner

AUTOINJECTOR WITH LOW ENERGY PLUNGER LOADING

CROSS-REFERENCE TO RELATED APPLICATIONS

The priority benefit of U.S. Provisional Patent Application No. 62/019,729, filed Jul. 1, 2014, is claimed, the entire contents of which are incorporated herein by reference.

FIELD

The present disclosure relates to injection devices for drug delivery. More particularly, the present disclosure relates to injection devices for drug delivery which include mechanisms for loading the plunger to reduce and/or eliminate shock during the operation thereof.

BACKGROUND

Autoinjectors and on-body injectors offer several benefits in delivery of therapeutics. One of the benefits can include simplicity of use, as compared with traditional methods of delivery using, for example, conventional syringes.

Many injector systems use coil and other spring structures to provide actuation energy for functions such as needle insertion and fluid delivery. The use of springs can offer benefits of simplicity and low cost, but can also have certain disadvantages.

There is a linear relationship between force and displacement in spring actuators. To provide sufficient energy for drug delivery at the end of plunger stroke, an excessive amount of energy may be input to the system as device activation or drug delivery commences.

Further, as higher viscosity drugs are delivered via autoinjectors, the requisite spring forces will likely increase. Springs with higher spring constants transmit more force to the drug product and primary container. Since kinetic energy is proportional to velocity squared, even incremental increases in the spring constant can result in large changes in the net kinetic energy applied to the drug and primary container and can prevent proper dose completion.

The patient may feel this excessive energy as a slap or similar physical bump, as the spring driven plunger impacts the stopper of the primary container storing the drug. Such mechanical bumps can also be distracting or disturbing to users of the injectors. It is therefore desirable to eliminate such potential disturbances.

Additionally, the slap and bump generated by the excessive energy can cause catastrophic effects, such as breakage of the primary container and drug product damage cause by shear load. Furthermore, high force springs can produce high shear rates on the drug product. In some cases, this high shear rate is undesireable.

Accordingly, an autoinjector is needed that can maintain the intended spring force load while reducing the transmitted force and resultant energy to the drug product, thereby reducing the potential for structural damage to the primary container or the injector itself. Such an autoinjector may be potentially more comfortable and safer to use, and applicable to a greater range of drugs.

SUMMARY

Disclosed herein are an injection device, methods and systems for drug delivery. Within this disclosure, reference may be made to "autoinjectors," however, such reference should also be understood to refer to on-body injectors where the description is applicable. In various embodiments, the device may comprise: a) a container having a stopper movably disposed in the container for expelling the drug; b) an injection drive mechanism comprising a plunger for acting on the stopper and a first energy source having a first selected potential energy for exerting a first force on the plunger to cause the plunger to act on the stopper to expel the drug; and c) a plunger loading mechanism for substantially preventing the plunger from accelerating to a predetermined velocity before it acts on the stopper. The plunger loading mechanism comprises a second energy source such as a container biasing member that may be a spring having a second selected potential energy applying a second force on the container and which reduces or eliminates the distance between the plunger and the stopper, prior to the plunger accelerating to the predetermined velocity. The second force of the second selected potential energy of the spring may be less than the first force of the first selected potential energy of the energy source of the drive mechanism. The container or reservoir may contain a medicament and can be a cartridge or prefilled syringe.

BRIEF DESCRIPTION OF THE DRAWINGS

The same reference numerals are used in the drawings to identify the same or similar elements and structures in the various embodiments.

DETAILED DESCRIPTION

Figure 1A:
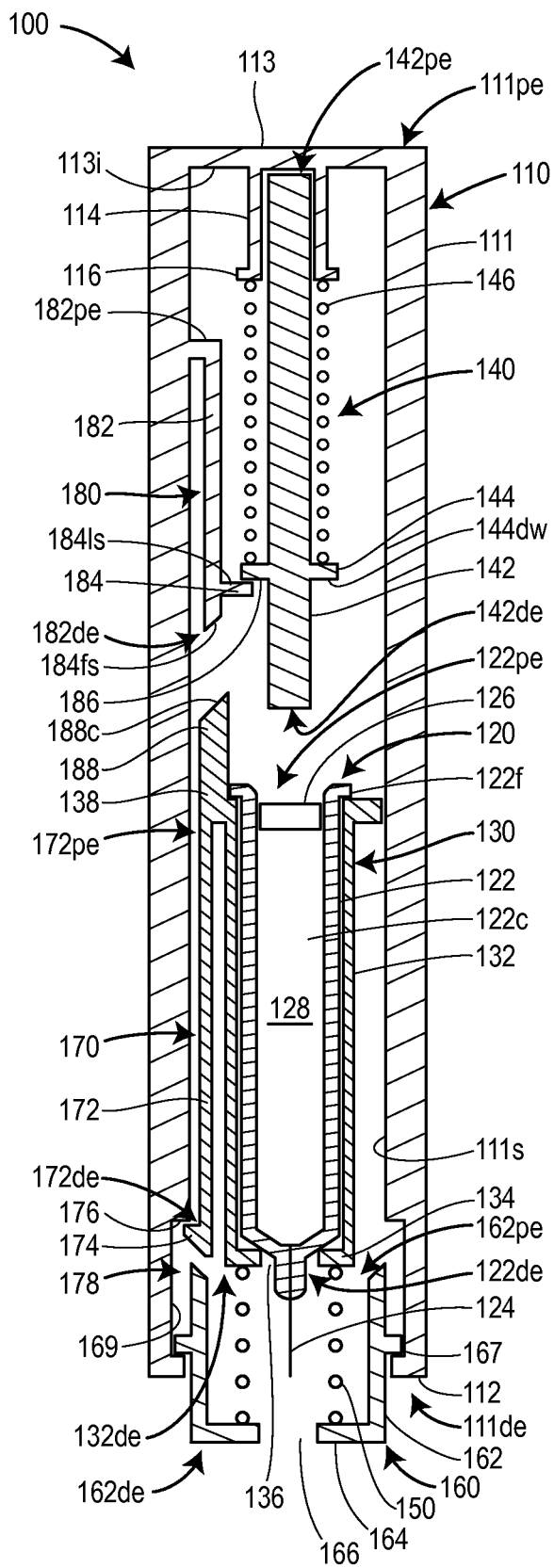
FIG. 1A is an elevational view in cross-section of an embodiment of an injection device for drug delivery according to the present disclosure.

Disclosed herein is an injection device for drug delivery. In one embodiment, the injection device comprises a container for storing a drug, the container comprising a stopper movably disposed in the container for expelling the drug; an injection drive comprising a plunger for acting on the stopper and first energy source having a first selected potential energy for exerting a first force on the plunger to cause the plunger to act on the stopper; and a structure hereinafter referred to as a "plunger loader." The plunger loader substantially prevents the plunger from accelerating to a predetermined velocity before it acts on the stopper.

In some embodiments the plunger loader has a second selected potential energy for generating a second force for reducing or eliminating a distance between the plunger and the stopper, prior to the plunger accelerating to the velocity.

In some embodiments a magnitude of the second force of the selected potential energy is less than a magnitude of the first force of the first selected potential energy.

In some embodiments, in an operational mode, the plunger loader reduces or eliminates the distance between the plunger and the stopper, prior to the plunger accelerating to the velocity.

In some embodiments, in an operational mode, the plunger loader causes the plunger and the stopper to engage (e.g., contact) one another, prior to the plunger accelerating to the velocity.

In some embodiments the injection device further comprises a dose delivery member for dispensing the drug from the container, wherein after the plunger loader reduces or eliminates the distance between the plunger and the stopper, the first force exerted on the plunger by the first energy source accelerates the plunger to the predetermined velocity as it acts on the stopper thereby causing the dose delivery member to penetrate body tissue of a patient.

In some embodiments the first force of the first selected potential energy of the energy source overcomes the second force of the second selected potential energy of the plunger loader to accelerate the plunger to the predetermined velocity.

In some embodiments after the dose delivery member penetrates the body tissue of the patient, the first force exerted on the plunger by the first energy source causes the plunger to drive the stopper through the container to expel the drug therefrom.

In some embodiments the first force exerted on the plunger by the first energy source causes the plunger to drive the stopper through the container to expel the drug therefrom.

In some embodiments the first force of the first selected potential energy of the energy source overcomes the second force of the second selected potential energy of the plunger loader to allow the first energy source to cause the plunger to drive the stopper through the container to expel the drug therefrom.

In some embodiments the second energy source of the plunger loader comprises a spring.

In some embodiments, the plunger loader directly or indirectly moves the container toward the injection drive mechanism, thereby reducing or eliminating the distance between the plunger and the stopper, prior to the plunger accelerating to the velocity.

In some embodiments the device further comprises a carrier for moving the container relative to the injection drive, wherein the plunger loader moves the carrier toward the injection drive thereby reducing or eliminating the distance between the plunger and the stopper, prior to the plunger accelerating to the velocity.

In some embodiments the device further comprises a carrier lock for preventing movement of the carrier when the device is in a ready-to-use mode and thereby maintaining the distance between the plunger and the stopper.

In some embodiments the carrier lock comprises a lock hook catch and a lock hook for releasably engaging the lock hook catch.

In some embodiments the carrier lock comprises a lock arm, the lock hook disposed on the lock arm.

In some embodiments the device further comprises an outer casing for encasing at least the carrier and the primary container, the outer casing including the lock hook catch.

In some embodiments the device further comprises a carrier lock release for unlocking the carrier lock.

In some embodiments the device further comprises a dose delivery member for dispensing the drug from the container and a needle guard for preventing contact with the dose delivery member, wherein the needle guard includes the carrier lock release.

In some embodiments the plunger loader is disposed between the needle guard and the carrier and container.

In some embodiments the carrier lock release includes a cam surface and the lock hook or the lock hook arm includes a cam following surface, the cam surface engaging the cam following surface to disengage the lock hook from the lock hook catch.

In some embodiments the device further comprises an injection drive lock for locking the injection drive.

In some embodiments the injection drive lock comprises a plunger lock hook catch and a plunger lock hook for releasably engaging the plunger lock hook catch.

In some embodiments the injection drive lock comprises a plunger lock arm, the plunger lock hook disposed on the plunger lock arm.

In some embodiments the plunger includes the plunger lock hook catch.

In some embodiments the device further comprises an injection drive lock release for unlocking the injection drive lock, thereby activating the injection drive.

In some embodiments the carrier includes the injection drive lock release.

In some embodiments, the guard includes the injection drive lock release.

In some embodiments the injection drive lock release includes a cam surface and the plunger lock hook or the plunger lock arm includes a cam following surface, the cam surface engaging the cam following surface to disengage the lock hook from the lock hook catch.

In some embodiments the first energy source comprises one or more springs.

In some embodiments the first energy source comprises a gas pressure or gas releasing arrangement.

In some embodiments the injection device further comprises a dose delivery member for dispensing the drug from the container.

In some embodiments the dose delivery member comprises an injection needle.

In some embodiments the container comprises a syringe.

In some embodiments the device further comprises a drug stored in the container.

In some embodiments the container is prefilled with a drug.

In some embodiments the injection device further comprises a spring for defining the axial location of at least one of the needle guard, the container and the carrier.

In some embodiments the injection device further comprises an outer casing including a tubular sidewall for encasing at least the carrier and the primary container and a needle guard for preventing contact with a dose delivery member associated with the container, wherein the plunger loader is disposed between the carrier and the outer casing, and the needle guard comprises a spring disposed between the guard and outer casing.

In some embodiments, the dose delivery member includes a stake for piercing a septum of the container.

In some embodiments the drug is selected from the group consisting of TNF inhibitors, antibodies to the calcitonin gene-related peptide receptor, colony stimulating factors, erythropoiesis stimulating agents, apelin receptor agonists, anti-thymic stromal lymphopoietin antibodies, anti-thymic stromal lymphopoietinreceptor antibodies, antibodies that bind human Proprotein Convertase Subtilisin/Kexin Type 9 and tissue inhibitors of metalloproteinases.

Further disclosed herein is a method for administering a drug. The method comprises providing a container containing a drug and a stopper movably disposed in the container for expelling the drug; acting on the stopper with a plunger driven by a first energy source having a first selected potential energy that exerts a first force on the plunger; and substantially preventing the plunger from accelerating to a predetermined velocity with a plunger loader that applies a second force to the container before the plunger acts on the stopper.

In some embodiments of the method the plunger loader generates a second force with the second selected potential energy for reducing or eliminating a distance between the plunger and the stopper, prior to the plunger accelerating to the velocity.

In some embodiments of the method the second force of the second selected potential energy is less than the first force of the first selected potential energy.

In some embodiments of the method the plunger loader comprises a spring.

FIG. 1A shows an embodiment of an injection device 100 according to the present disclosure. The injection device 100 can be adapted as a single-use, disposable injector or a multiple-use reusable injector. The injection device 100 can be adapted to deliver any suitable medicament or drug including those having a high viscosity. Further, the injection device 100 can be adapted as an autoinjector for self-administration, although the injection device 100 can of course be used by a caregiver or a formally trained healthcare provider to administer an injection.

Referring still to FIG. 1A, the injection device 100 can comprise an elongated, housing or outer casing 110. The injection device 100 can further comprise a drug storage device 120 which can be a syringe, a drug storage device carrier 130, an injection drive mechanism (injection drive) 140, a plunger loading mechanism (plunger loader) 150, a needle guard 160, a carrier lock mechanism (carrier lock) 170, and an injection drive lock (injection drive lock) mechanism 180. One or more of the drug storage device 120, the carrier 130, the injection drive mechanism 140, the plunger loading mechanism 150, the guard 160, the carrier lock mechanism 170, and the injection drive lock mechanism 180 may be enclosed or partially enclosed in a part of the outer casing 110.

The outer casing 110 can be a single, unitary component or a multiple component assembly comprising a tubular sidewall 111 closed at a distal end 111*de* by a first end wall 112 and closed at a proximal end 111*pe* by a second end wall 113. The needle guard 160 can also be considered to be part of the outer casing 110, as it too defines an outer boundary of the device 100. A tubular support member 114 may extend from an interior surface 113*i* of the second end wall 113 for slidably supporting the injection drive mechanism 140. The free end of the tubular support member 114 may include a spring seat comprising, for example, an outwardly extending flange 116 surrounding the opening thereof.

Referring still to FIG. 1A, the drug storage device 120 can include a primary container 122, a dose delivery member 124, which can be an injection needle, canula or any other fluid dispensing element suitable for injecting a drug into the body, and a stopper 126. The primary container 122 may be an elongated tubular member having a closed distal end 122*de* and an open proximal end 122*pe*. The primary container 122 can further include an interior chamber 122*c* for storing one or more doses of a medicament or drug 128. In some embodiments, the interior chamber 122*c* of the primary container 122 may be prefilled with the one or more doses of the medicament or drug 128. The primary container 122 can include an outwardly extending flange 122*f* disposed at or adjacent to the open proximal end 122*pe* of the primary container 122. The flange 122*f* may be used by the drug storage device carrier 130 for supporting the drug storage device 120 in or on the carrier 130.

As shown in FIG. 1A, the dose delivery member 124 can extend through the closed distal end 122*de* of the primary container 122 and into the interior chamber 122*c* thereof, for dispensing a dose of the medicament or drug 128. A removable shield (not shown) can be installed over the dose delivery member 124 for maintaining same in a sterile state prior to use of the injection device 100.

Still referring to FIG. 1A, the stopper 126 of the drug storage device 120 can be disposed in the interior chamber 122*c* of the primary container 122 so that it is axially moveable relative to the primary container 122 for expelling the medicament or drug 128 through the dose delivery member 124. Some embodiments, the drug storage device 120 may comprise a conventional glass or plastic syringe or cartridge.

As shown in FIGS. 2A-2F, the drug storage device carrier 130 can be configured to be proximally and distally movable within the outer casing 110. The plunger loading mechanism 150 causes the proximal movement P of the carrier 130 within the outer casing 110 (FIGS. 2B and 2C) prior to the activation of the injection drive mechanism 140. When triggered, as will be described, the plunger loader 150 substantially reduces or eliminates the distance d between the stopper 126 of the drug storage device 120 and the injection drive mechanism 140 (FIGS. 2A and 2C), thereby reducing the force and resultant energy transmitted by the injection drive mechanism 140 to the drug product 128, drug storage device 120, and/or injection device 100. The injection drive mechanism 140 causes the distal movement of the carrier 130, which results in the insertion of the dose delivery member 124 into the body tissue BT of the patient.

Referring again to FIG. 1A, the drug storage device carrier 130 can comprise a sleeve 132 for receiving and fixedly holding the drug storage device 120 therein. The sleeve 132 may be closed at a distal end 132*de* by an end wall 134. The end wall 134 of the sleeve 132 may be configured to support the distal end 122*de* of the primary container 122 of the drug storage device 120. The end wall 134 of the sleeve 132 may include an aperture 136 which allows the dose delivery member 124 to extend through the end wall 134. In addition or alternatively, the proximal end surface of the sleeve 132 may be configured to support the proximal end of the drug storage device 120 via the flange 122*f* of the primary container 122. The drug storage device carrier 130 may further comprise an injection drive lock release mechanism 188 (plunger lock release 188) for releasing or unlocking the injection drive lock mechanism 180. The plunger lock release 188 can comprise a rod-like member which extends proximally from a protuberance 138 on the sleeve 132.

Referring still to FIG. 1A, the injection drive mechanism 140 can include a plunger rod 142 and a high energy source 146 (first energy source) for propelling or driving the plunger 142 to perform needle insertion and dose delivery. The proximal end 142*pe* of the plunger rod 142 may be supported in the tubular support member 114 of the outer casing 110 when the injection device 100 is armed or in a ready-to-use mode. The plunger rod 142 may include a spring seat comprising, for example, an annular ledge 144 disposed adjacent to or at the distal end 142*de* of the plunger rod 142.

The high energy source 146 may comprise a biasing member such as one or more coil spring elements, as depicted in FIG. 1A. The plunger rod 142 can extend through the high energy coil spring 146 with one end of the spring 146 seated on the annular ledge 144 and the other end of the spring 146 is seated on the flange 116 of the tubular support member 114. Prior to operation of the injection device 100, the high energy coil spring 146 may be compressed between the annular ledge 144 of the plunger rod 142 and the flange 116 of the tubular support member 114, thereby applying a spring biasing force (a first force) to the plunger rod 142. When the injection device 100 is activated, as will be explained further on, the high energy coil spring 146 expands in the distal direction, thereby propelling the plunger rod 142 distally through the drug storage device 120, thereby driving the stopper 126 through the primary container 122 to expel the drug 128 through the dose delivery member 124.

In other embodiments, the high energy source 146 can alternatively or further include a gas pressure or gas releasing arrangement. The energy provided by gas pressure or gas releasing arrangement operates on the plunger rod 142 to propel it into the drug storage device 120, thereby driving the stopper 126 through the primary container 122 to expel the drug 128 through the dose delivery member 124.

The plunger loading mechanism 150 reduces the transmitted force and resultant energy to the drug product 128, thereby reducing the physical disturbance experienced by the user and the potential for structural damage to the drug storage device 120 and the injection device 100. As shown in FIG. 1A, the plunger loading mechanism in various embodiments may comprise a low energy source 150 (second energy source), which too can include a biasing member such as the depicted coil spring. The low energy spring 150 can have a second selected potential energy or spring rate that generates a second force that has a magnitude that is less than a magnitude of the first force generated by the first selected potential energy or spring rate of the high energy source 146 of the injection drive mechanism 140. The second energy source of the plunger loading mechanism 150 is not limited to one coil spring, as depicted, and may comprise multiple coil springs, coil springs having variable spring rates, leaf and other types of springs and other biasing mechanisms.

During the operational mode of the device 100, the plunger loading mechanism 150 may reposition the drug storage device carrier 130 in the outer casing 110 such that the distance d between the plunger rod 142 of the injection drive mechanism 140 and the stopper 126 of the drug storage device 120 is substantially reduced or eliminated, prior to activation of the injection drive mechanism 140. In other embodiments, in the operational mode, the plunger loading mechanism 150 may reposition the drug storage device carrier 130 in the outer casing 110 such that initial contact takes place between the plunger rod 142 and the stopper 126, prior to activation of the injection drive mechanism 140.

Referring still to FIG. 1A, the guard 160 may comprise an axially movable member disposed at the distal end 111*de* of the tubular sidewall of the outer casing 110. The guard 160 may be configured to activate the processes which cause the injection device 100 to administer an injection when the guard 160 is engaged with a patient's body tissue at a selected injection site and the device 100 is pressed toward the injection site, as will be explained further on. The guard 160 can also prevent one from contacting the dose delivery member 124 after the injection has been completed and the device 100 has been removed from the injection site. The guard 160 in various embodiments may comprise a cylindrical sidewall 162 which is open at a proximal end 162*pe* and which is closed at a distal end 162*de* by an end wall 164. The end wall 164 may include an opening 166 that allows the dose delivery member 124 of the drug storage device 120 to extend therethrough during the injection process. The guard 160 may further comprise a stop rib 167 disposed on the outer surface of the sidewall 162 of the guard 160, which traverses a continuous annular groove 169 formed in the interior sidewall surface 111*s* of the outer casing 110, adjacent to the distal end 111*de* thereof. The stop rib 167 and groove 169 operate to limit the distal and proximal movement of the guard 160 and prevents it from being withdrawn from the outer casing 110. The guard 160 can further comprise a carrier lock release mechanism 178 formed at the proximal end 162*pe* of the guard sidewall 162 for unlocking or releasing the carrier lock mechanism 170. The low energy spring 150 can be disposed between the end wall 164 of the guard 160 of the outer casing and the distal end wall 134 of the carrier sleeve 132. The lower energy/spring rate of the low energy spring 150 allows it to hold the guard 160 in an extended position relative to the outer casing 110, when the injection device 100 is armed or in the ready-to-use mode (i.e., prior to use of the injection device 100 to administer an injection), and also allows it to be compressed between the guard 160 and the carrier sleeve end wall 134 by the high energy source 146 driven plunger 142 of the injection drive mechanism 140 during operation.

Referring still to FIG. 1A, the carrier lock mechanism 170 may comprise a flexible cantilever lock arm (carrier lock arm) 172, a carrier lock hook 174, and a carrier lock hook catch 176. The carrier lock arm 172 may have a proximal end 172*pe* coupled to the protuberance 138 formed on the sleeve 132 of the drug storage device carrier 130 and extends distally therefrom.

Figure 1B:
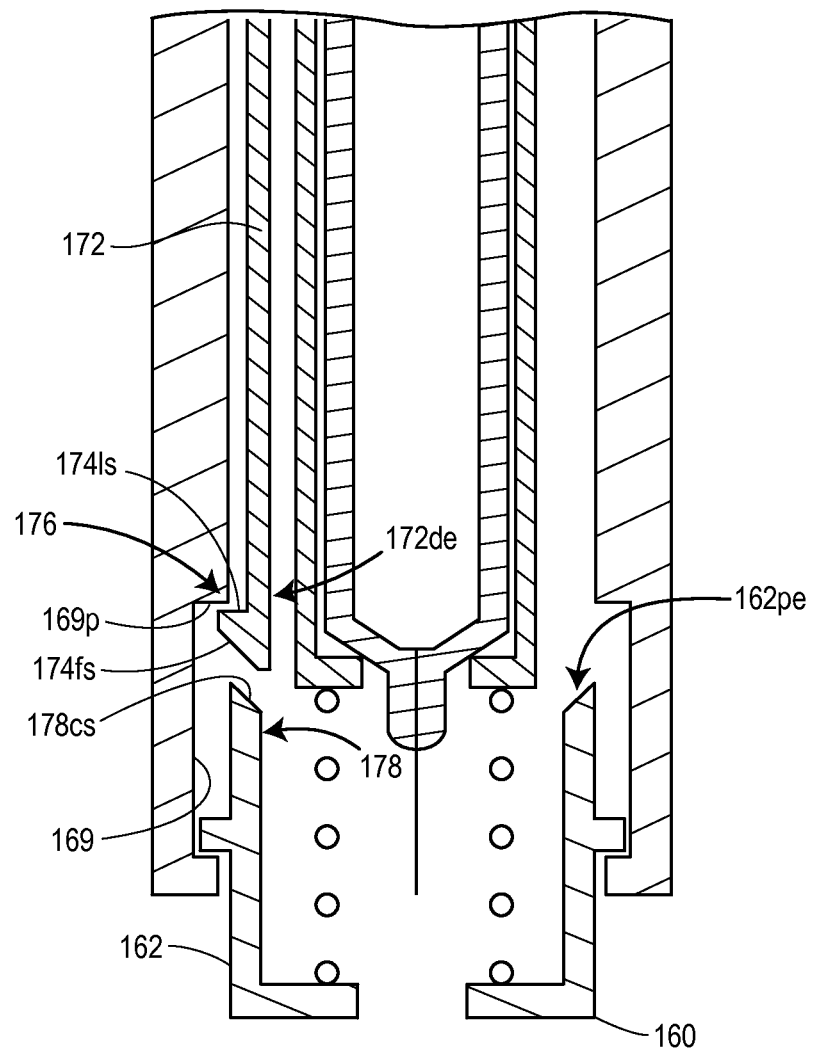
FIG. 1B is an enlarged view of a distal end of the injection device shown in FIG. 1A.

As shown in FIG. 1B, the carrier lock hook 174 may be disposed at a free distal end 172*de* of the carrier lock arm 172. The carrier lock hook 174 can include a proximal lock surface 174*ls* and an outward and distally facing inclined cam follower surface 174*fs* which extends distally from the proximal lock surface 174*ls*. The carrier lock hook catch 176 can be formed by a proximal side wall 169*p* of the outer casing groove 169. The proximal end 162*pe* of the guard sidewall 162 forming the carrier lock release 178 may include an inward and proximally facing inclined cam surface 178*c*, which is complementary to and engages the inclined cam follower surface 174*fs* of the carrier lock hook 174 to release or unlock of the carrier lock mechanism 170.

Although not shown, other embodiments of the carrier lock mechanism may include multiple carrier lock arms and carrier lock hooks. Further, the groove defining the carrier lock hook catch 176 may comprise an annular array of individual segments that each receive a corresponding one of the carrier lock hooks 174, instead of being configured as a single continuous annular groove, as described earlier.

Referring again to FIG. 1A, the injection drive lock mechanism 180 may comprise a flexible cantilever lock arm (plunger lock arm) 182, a plunger lock finger 184, and a plunger lock finger catch 186. The plunger lock arm 182 may have a proximal end 182*pe* coupled to the interior sidewall surface 111*s* of the outer casing 110. The plunger lock finger 184 may be disposed above the distal end 182*de* of the plunger lock arm 182. The distal end 182*de* of the plunger lock arm 182 can define an inward and distally facing inclined cam follower surface 184*fs*. The plunger lock finger catch 186 can comprise a distal wall 144*dw* of the annular ledge 144 of the plunger rod 142. The plunger lock release 188 may include an outwardly and proximally facing inclined cam surface 188*c*, which is complementary to and engages the inclined cam follower surface 184*fs* of the plunger lock arm 182 to the release or unlock of the injection drive lock mechanism 180.

Although not shown, other embodiments the plunger lock finger 184 and the cam follower surface 184*fs* can be combined into a structure similar to the carrier lock hook 174.

Prior to use and/or when the injection device 100 is armed or in the ready-to-use mode, the guard 160 may be fully extended, the drug storage device carrier 130 may be locked in a needle concealed position by the locked carrier lock mechanism 170, and the injection drive mechanism 140 may be locked in an armed position by the locked injection drive lock mechanism 180, as shown for example in FIG. 1A.

Figure 2A:
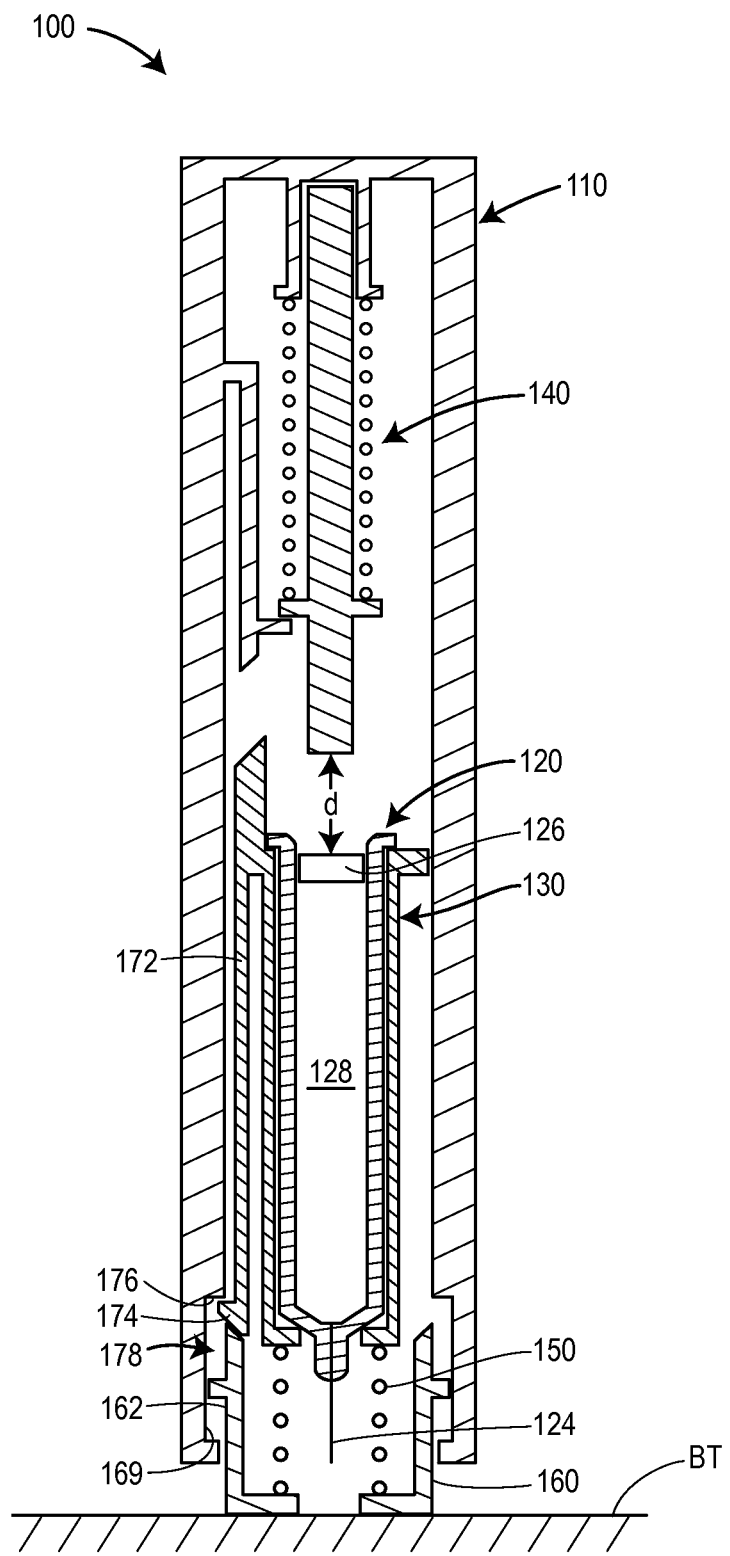
FIGS. 2A-2F are elevational views in cross-section illustrating various operational modes of the injection device of FIGS. 1A and 1B according to an embodiment of the present disclosure.

FIGS. 2A-2F illustrate the operation of the injection device 100 to administer an injection, according to an embodiment. FIG. 2A shows the injection device 100 after the guard 160 of the device 100 has been placed on a patient's body tissue BT (e.g., skin) at a selected injection site and the device has been pressed partially toward the body of the patient to commence an injection. During this phase of operation, the low energy spring 150 compresses easily to allow the guard 160 to move proximally P into the outer casing 110. As this takes place, the inclined cam surface 178*cs* (FIG. 1B) of the carrier lock release mechanism 178 defined by the relatively rigid guard sidewall 162, engages the complementary inclined cam follower surface 174*fs* (FIG. 1B) of the carrier lock hook 174 of the carrier lock mechanism 170. As the guard 160 moves further proximally P into the outer casing 110, the flexible carrier lock arm 172 bends away from the interior sidewall surface 111*s* of the outer casing 110 as the inclined cam follower surface 174*fs* (FIG. 1B) of the carrier lock hook 174 slides along the complementary inclined cam surface 178*cs* (FIG. 1B) of the carrier lock release mechanism 178, thereby disengaging or releasing the lock surface 174*ls* (FIG. 1B) of the carrier lock hook 174 from the carrier lock hook catch 176 to unlock the carrier lock mechanism 170, thereby activating the plunger loading mechanism 150.

Figure 2B:
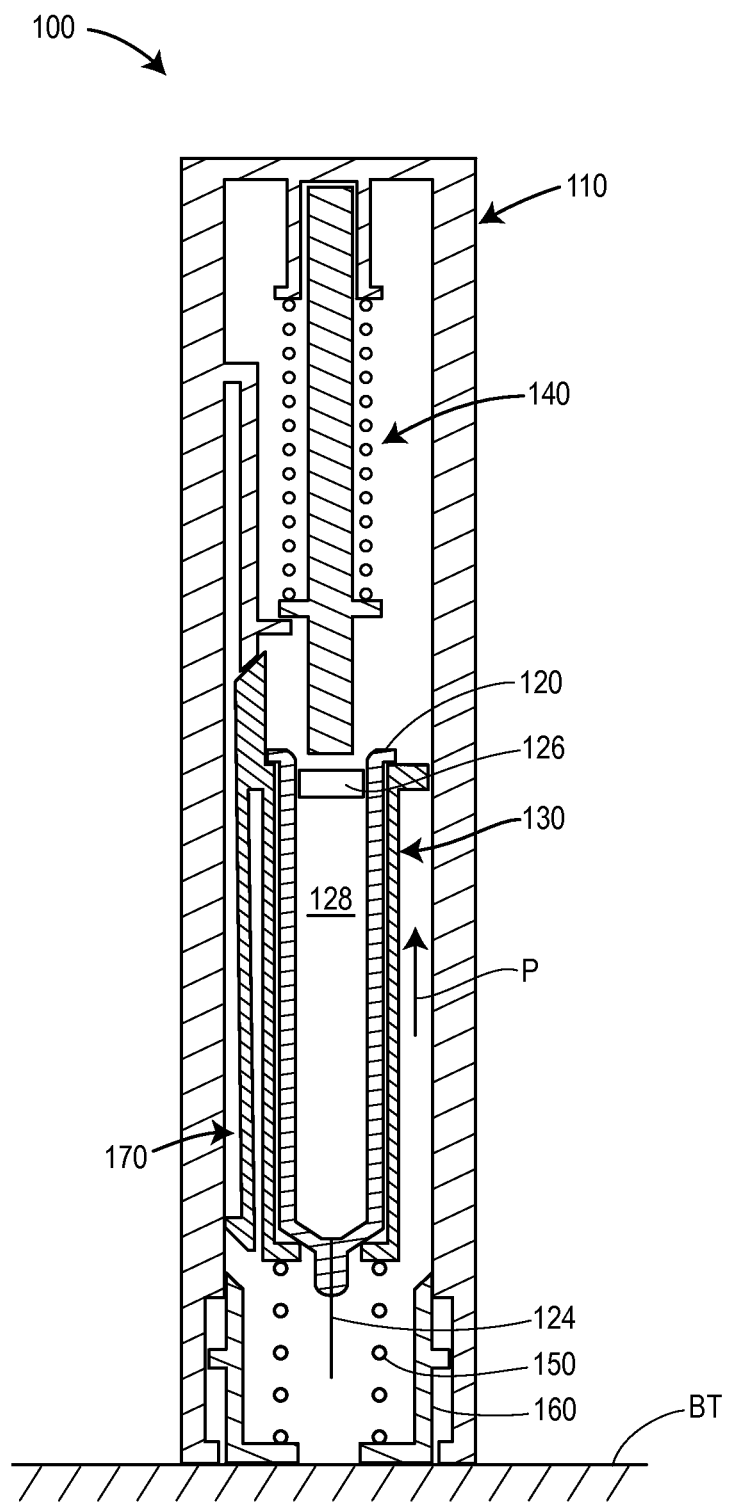

FIG. 2B shows the injection device 100 after the plunger loading mechanism 150 has been activated, such that the device 100 occupies the operational mode. During this phase of operation, the low energy spring 150 starts to expand, thereby moving (e.g., urging) the drug storage device carrier 130 containing the drug storage device 120 proximally P toward the injection drive mechanism 140, thereby reducing the distance d between the plunger 142 and the stopper 126.

Figure 2C:
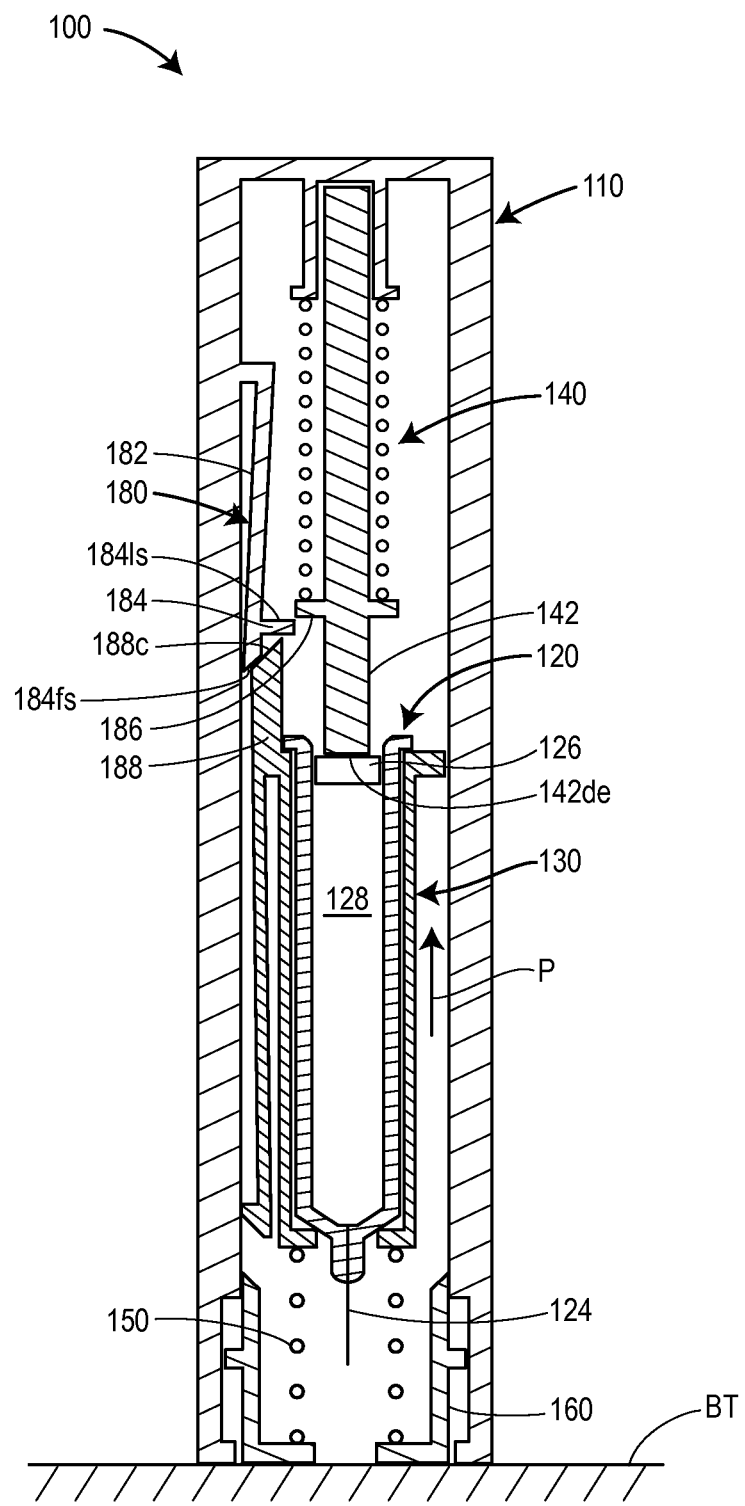

FIG. 2C shows the injection device 100 in a further operational mode after the drug storage device carrier 130, driven by the low energy spring 150, has reached its proximal-most position within the outer casing 110 and the plunger lock release 188 has released or unlocked the injection drive lock mechanism 180. With the drug storage device carrier 130 at the proximal-most position, the distal end of the plunger rod 142 engages or is spaced only slightly from the stopper 126 of the drug storage device 120. During the injection drive lock release operation, the inclined cam surface 188*c* of the relatively rigid plunger lock release 188 engages the complementary inclined cam follower surface 184*fs* of the plunger lock finger 184. As the drug storage device carrier 130 moves to its proximal-most position, the flexible plunger lock arm 182 bends away from the injection drive mechanism 140, as the inclined cam follower surface 184*fs* of the plunger lock arm 182 slides along the complementary inclined cam surface 188*c* of the plunger lock release 188, thereby disengaging or releasing the plunger lock finger 184 of the plunger lock arm 182 from the plunger lock finger catch 186, to unlock the injection drive lock mechanism 180, thereby activating the injection drive mechanism 140.

Figure 2D:
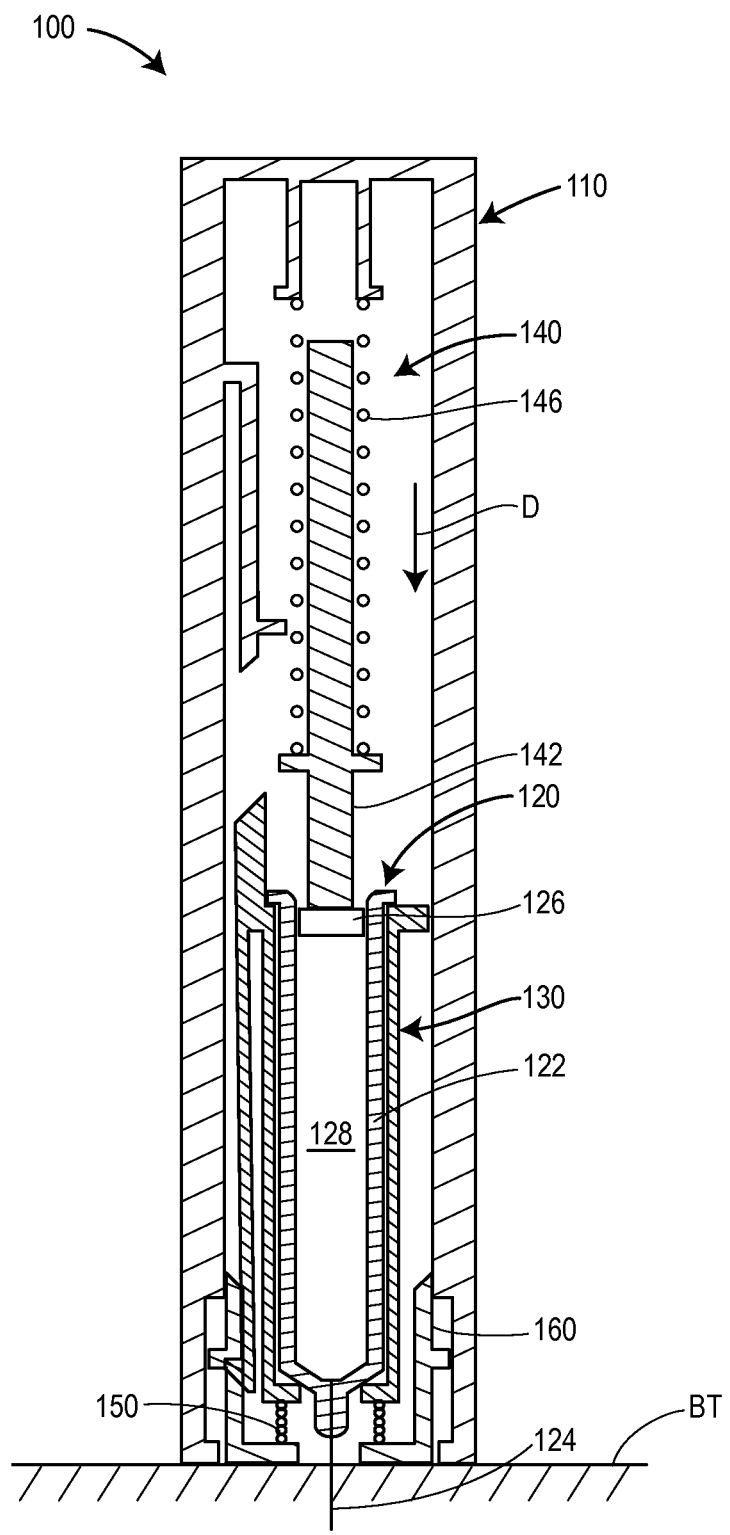

FIG. 2D shows the injection device 100 after the plunger rod 142, propelled (e.g., urged) by the high energy source 146, has driven the drug storage device carrier 130 to its distal-most position, which causes the dose delivery member 124 to penetrate the body tissue BT of the patient at the injection site (e.g., via the partially expanded high energy spring 146). During this phase of the injection, the high energy source 146 of the injection drive mechanism 140 overcomes the low energy spring 150 and compresses it as it propels the plunger rod 142, which drives drug storage device carrier 130 distally D to its distal-most position to achieve dose delivery member 124 penetration of the body tissue BT of the patient.

Figure 2E:
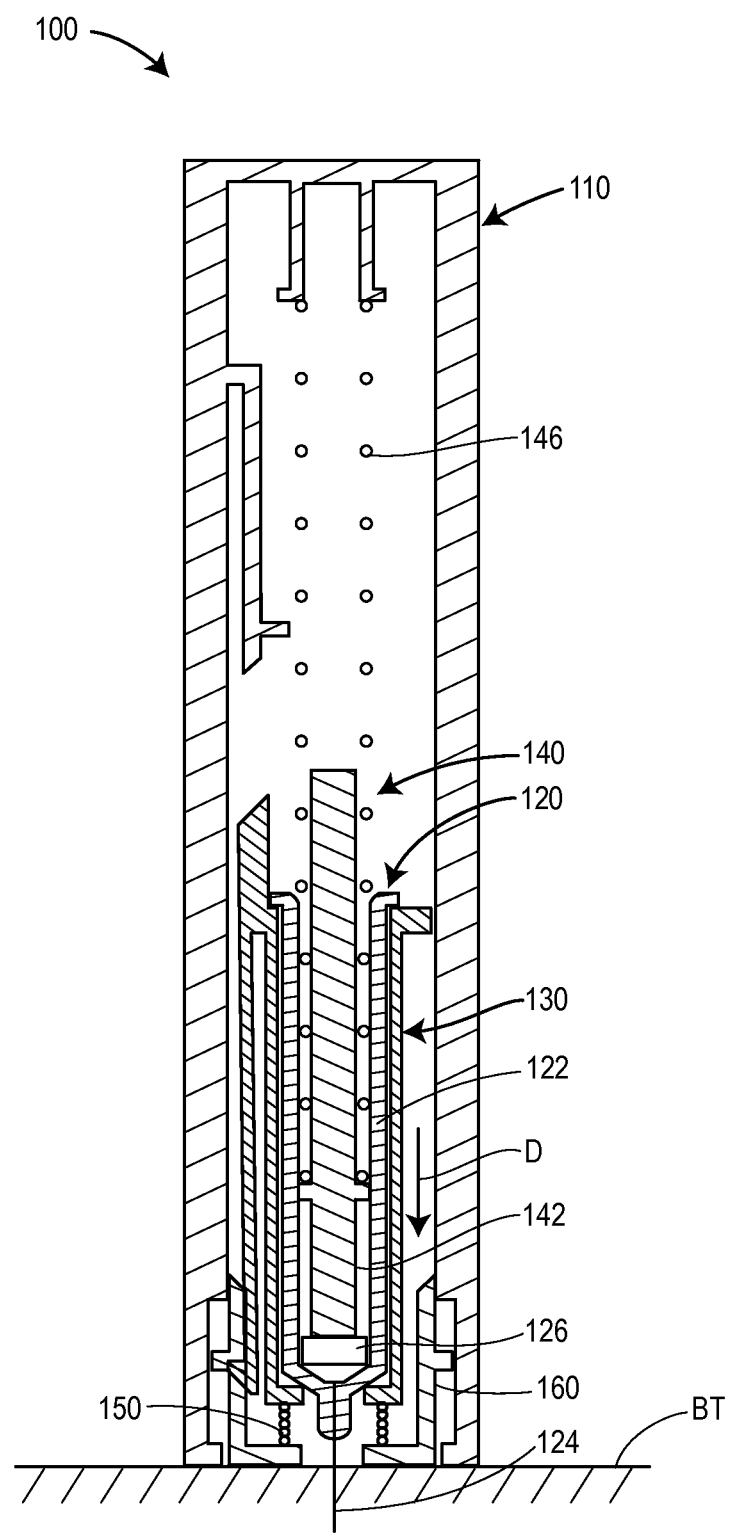

As shown in FIG. 2E, the high energy source 146 continues propel (e.g., urge) the plunger rod 142 distally D to drive the stopper 126 of the drug storage device 120 through the primary container 122, to expel the drug 128 therefrom and through the dose delivery member 124, thereby delivering the drug 128 to the patient and completing the injection (e.g., via the expanded high energy spring 146).

Figure 2F:
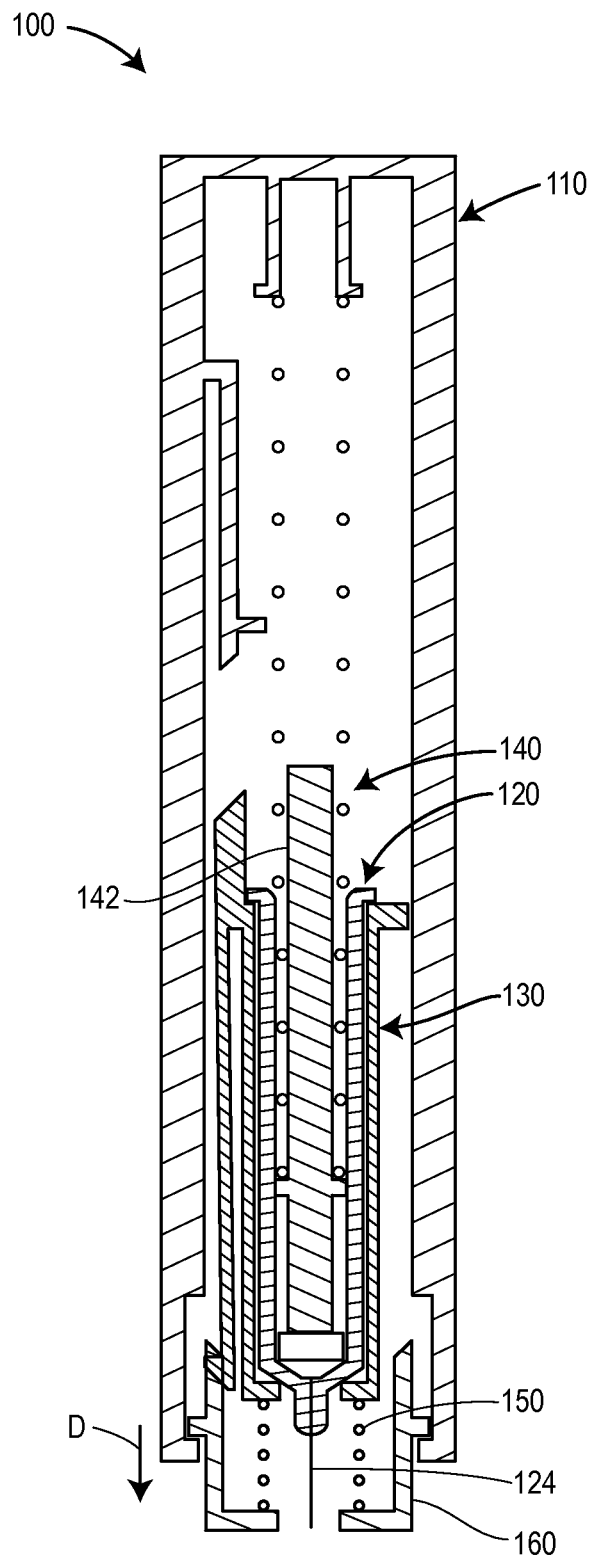

FIG. 2F shows the injection device 100 after the dose delivery member 124 has been withdrawn from the body tissue BT of the patient at the injection site. As shown, the low energy spring 150 has expanded partially to move the guard 160 distally D to the extended position so that it covers the dose delivery member 124, to prevent contact therewith.

The kinetic energy applied by the plunger 142 to the drug 128, the drug storage device 120, and/injector can be as high as ~0.11 Joules. By reducing or eliminating the distance d between the stopper and the plunger rod 142 before activating the injection drive mechanism 140, the plunger loading mechanism 150 substantially reduces or eliminates the kinetic energy applied by the plunger 142 to the drug 128, the drug storage device 120, and/injector by limiting the velocity of the plunger rod 142, prior to contacting the stopper 126 or causing the stopper 126 and plunger rod 142 to contact each other prior to activating the plunger driver mechanism 140 (i.e., where the velocity of the plunger rod 142 is approximately zero (0)). Accordingly, the plunger loading mechanism ensures that pressure delivered by the plunger to the drug product does not induce syringe breakage, cause appreciable "slap" or discomfort to the patient, and/or prevents shear forces from damaging the drug product. In various embodiments the plunger loading mechanism can be adapted to reduce the kinetic energy applied by the plunger by less than 1%. In other embodiments the plunger loading mechanism can be adapted to reduce the kinetic energy applied by the plunger by about 1-5%. In further embodiments the plunger loading mechanism can be adapted to reduce the kinetic energy applied by the plunger by about 5-10%. In still further embodiments the plunger loading mechanism can be adapted to reduce the kinetic energy applied by the plunger by about 5-10%. In still further embodiments the plunger loading mechanism can be adapted to reduce the kinetic energy applied by the plunger by about 10-15%. In still further embodiments the plunger loading mechanism can be adapted to reduce the kinetic energy applied by the plunger by about 15-20%. In yet further embodiments the plunger loading mechanism can be adapted to reduce the kinetic energy applied by the plunger by about 20-30%. In yet further embodiments the plunger loading mechanism can be adapted to reduce the kinetic energy applied by the plunger by about 30-50%. In yet further embodiments the plunger loading mechanism can be adapted to reduce the kinetic energy applied by the plunger by about 51%-100%.

In various embodiments, the plunger loading mechanism can be adapted to limit the peak dynamic pressure in the drug storage device to 8.5 MPa±1%. In various other embodiments, the plunger loading mechanism can be adapted to limit the peak dynamic pressure in the drug storage device to 8.5 MPa±5%. In various other embodiments, the plunger loading mechanism can be adapted to limit the peak dynamic pressure in the drug storage device to 8.5 MPa±10%. In various other embodiments, the plunger loading mechanism can be adapted to limit the peak dynamic pressure in the drug storage device to 8.5 MPa±15%. In various other embodiments, the plunger loading mechanism can be adapted to limit the peak dynamic pressure in the drug storage device to 8.5 MPa±20%. In various other embodiments, the plunger loading mechanism can be adapted to limit the peak dynamic pressure in the drug storage device to 8.5 MPa±25%. In various other embodiments, the plunger loading mechanism can be adapted to limit the peak dynamic pressure in the drug storage device to 8.5 MPa±30%. In various other embodiments, the plunger loading mechanism can be adapted to limit the peak dynamic pressure in the drug storage device to 8.5 MPa±35%. In various other embodiments, the plunger loading mechanism can be adapted to limit the peak dynamic pressure in the drug storage device to 8.5 MPa±40%. In various other embodiments, the plunger loading mechanism can be adapted to limit the peak dynamic pressure in the drug storage device to 8.5 MPa±45%. In various other embodiments, the plunger loading mechanism can be adapted to limit the peak dynamic pressure in the drug storage device to 8.5 MPa±50%.

In still various other embodiments the peak dynamic pressure in the drug storage device can be limited to a value in the range of approximately 3.5 MPa to approximately 9.5 MPa. In various other embodiments the peak dynamic pressure in the drug storage device can be limited to approximately 3.5 MPa, 3.6 MPa, 3.7 MPa, 3.8 MPa, 3.9 MPa, 4.0 MPa, 4.1 MPa, 4.2 MPa, 4.3 MPa, 4.4 MPa, or 4.5 MPa. In various other embodiments the peak dynamic pressure in the drug storage device can be limited to 5 MPa. In various other embodiments the peak dynamic pressure in the drug storage device can be limited to 5.5 MPa, In various other embodiments the peak dynamic pressure in the drug storage device can be limited to 6.0 MPa, In various other embodiments the peak dynamic pressure in the drug storage device can be limited to 6.5 MPa. In various other embodiments the peak dynamic pressure in the drug storage device can be limited to 7.0 MPa. In various other embodiments the peak dynamic pressure in the drug storage device can be limited to 7.5 MPa. In various other embodiments the peak dynamic pressure in the drug storage device can be limited to 8.0 MPa. In various other embodiments the peak dynamic pressure in the drug storage device can be limited to 8.5 MPa. In various other embodiments the peak dynamic pressure in the drug storage device can be limited to 9.0 MPa. In various other embodiments the peak dynamic pressure in the drug storage device can be limited to 9.5 MPa.

The reduction in the kinetic energy applied by the plunger 142 be can selected to prevent a physical disturbance and/or discomfort to the patient and/or user by preventing appreciable "slap," and/or reduce breakage of the drug storage device 120, and/or reduce drug product damage caused by shear load, and/or allow the injection device 100 to be used for injecting drugs with higher viscosities.

Figure 3:
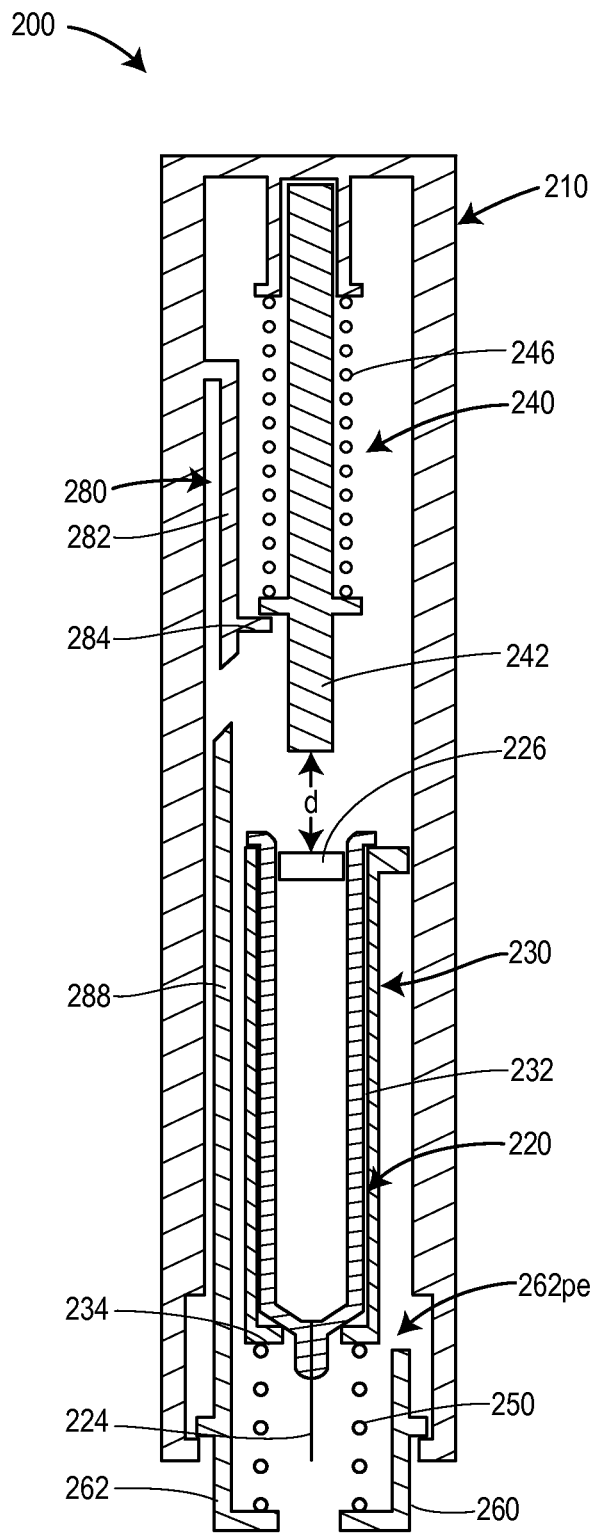
FIG. 3 is an elevational view in cross-section of another embodiment of the injection device according to the present disclosure.

FIG. 3 shows another embodiment of the injection device 200 according to the present disclosure. The injection device 200 is similar to the device 100, as the injection device 200 may comprise an outer casing 210, a drug storage device 220, a drug storage device carrier 230, an injection drive mechanism 240, a plunger loading mechanism 250, a guard 260, and an injection drive lock mechanism 280, which are similar in structure and function to the corresponding components described with respect to the device 100 of FIG. 1. The injection device 200, however, differs from the injection device 100 of FIG. 1A, in that the drug storage device carrier 230 does not have the carrier lock mechanism, but may comprise a sleeve 232 for receiving and fixedly holding the drug storage device 220 therein as described earlier with respect to the device 100.

Further, the guard 260 of the device 200 may be configured to include an injection drive lock release mechanism 288. As shown in FIG. 3, the guard 260 may be configured to include an injection drive lock release mechanism 288 that extends proximally from the proximal end 262pe of the guard sidewall 262, which is configured to unlock or release the injection lock mechanism 270. As described earlier with respect to the device 100 of FIG. 1A, the low energy spring 250 of the device 200 can be disposed between the end wall 264 of the guard 260 and the distal end wall 234 of the carrier sleeve 232, and functions as the plunger load mechanism. The lower energy/spring rate of the low energy spring 250 allows it to hold the guard 260 in an extended position relative to the outer casing 210, when the injection device 200 is armed or in a ready-to-use mode (i.e., prior to use of the injection device 200 to administer an injection), and also allows it to be compressed between the guard 260 and the carrier sleeve end wall 234 by the high energy source driven plunger 242 of the injection drive mechanism 240.

Figure 4A:
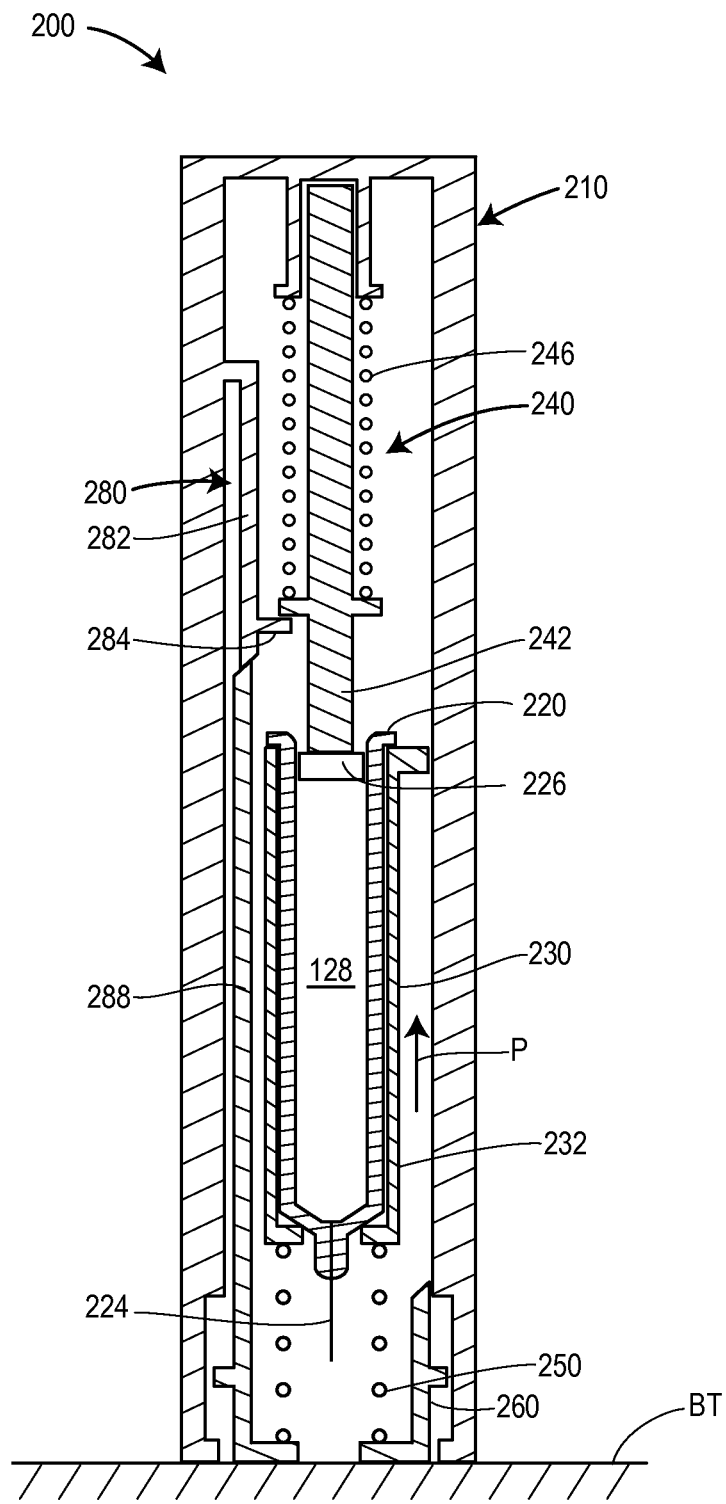
FIGS. 4A and 4B are elevational views in cross-section illustrating various operational modes of the injection device of FIG. 3 according to an embodiment of the present disclosure.

As shown in FIG. 4A, during the operation of the device 200, the plunger loading mechanism 250 drives and repositions the drug storage device carrier 230 in the outer casing 210 such that the distance d (FIG. 3) between the plunger rod 242 of the injection drive mechanism 240 and the stopper 226 of the drug storage device 220 is substantially reduced or eliminated by causing initial contact between the plunger rod 242 and the stopper 226, prior to activation of the injection drive mechanism 240.

Just as the drug storage device carrier 230 reaches its proximal-most position within the outer casing 210, the injection drive lock release mechanism 288 unlocks the injection drive lock mechanism 280, thereby activating the injection drive mechanism 240. The plunger rod 242, propelled by the high energy source 246, overcomes the low energy spring 250 and drives the drug storage device carrier 130 to its distal-most position, which causes the dose delivery member 224 to penetrate the body tissue BT of the patient at the injection site.

Figure 4B:
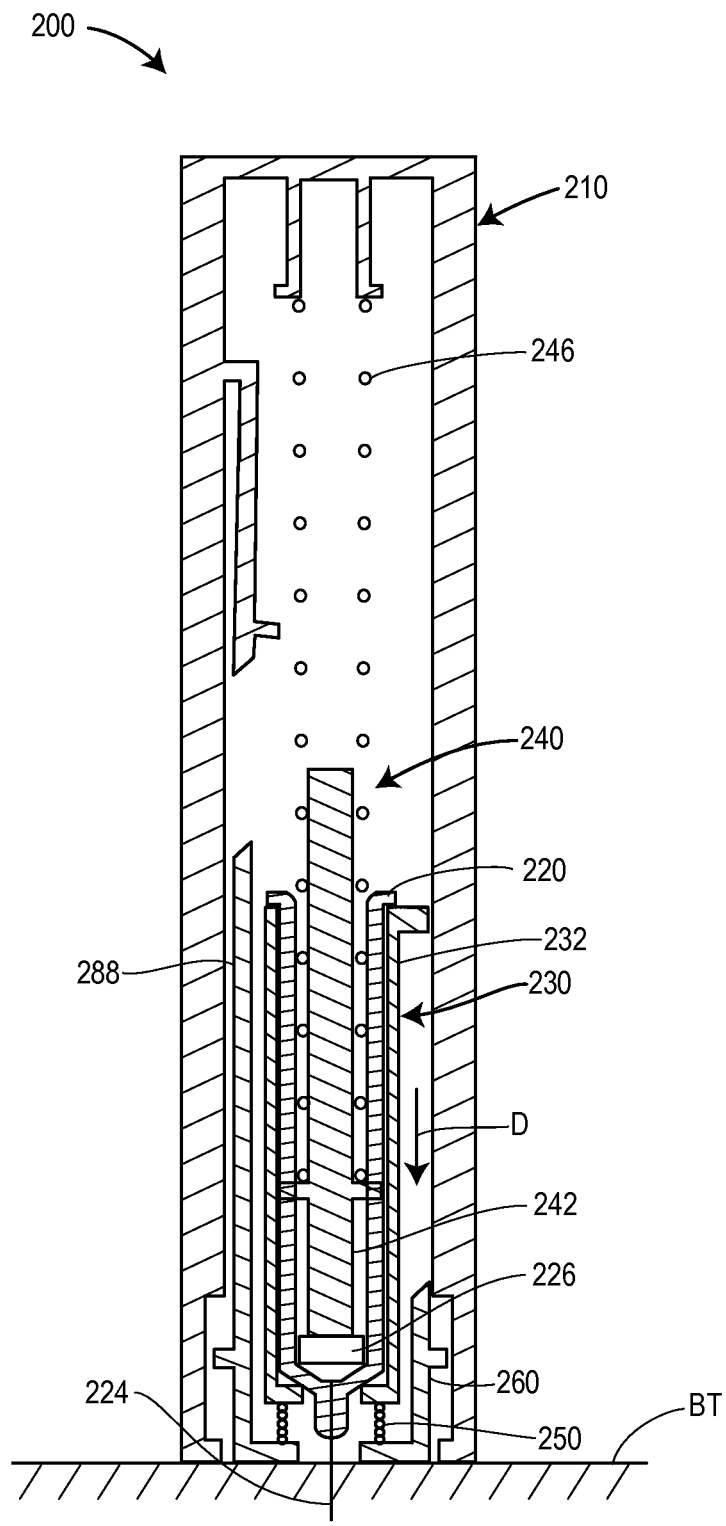

As shown in FIG. 4B, the high energy source 246 continues propel the plunger rod 242 distally D to drive the stopper 226 of the drug storage device 220 through the primary container 222, to expel the drug 228 therefrom and through the dose delivery member 224, thereby delivering the drug 228 to the patient and completing the injection. As the dose delivery member 224 is withdrawn from the body tissue BT of the patient at the injection site, the low energy spring 250 expands partially to move the guard 260 distally to the extended position so that it covers the dose delivery member 224, to prevent contact therewith.

Figure 5:
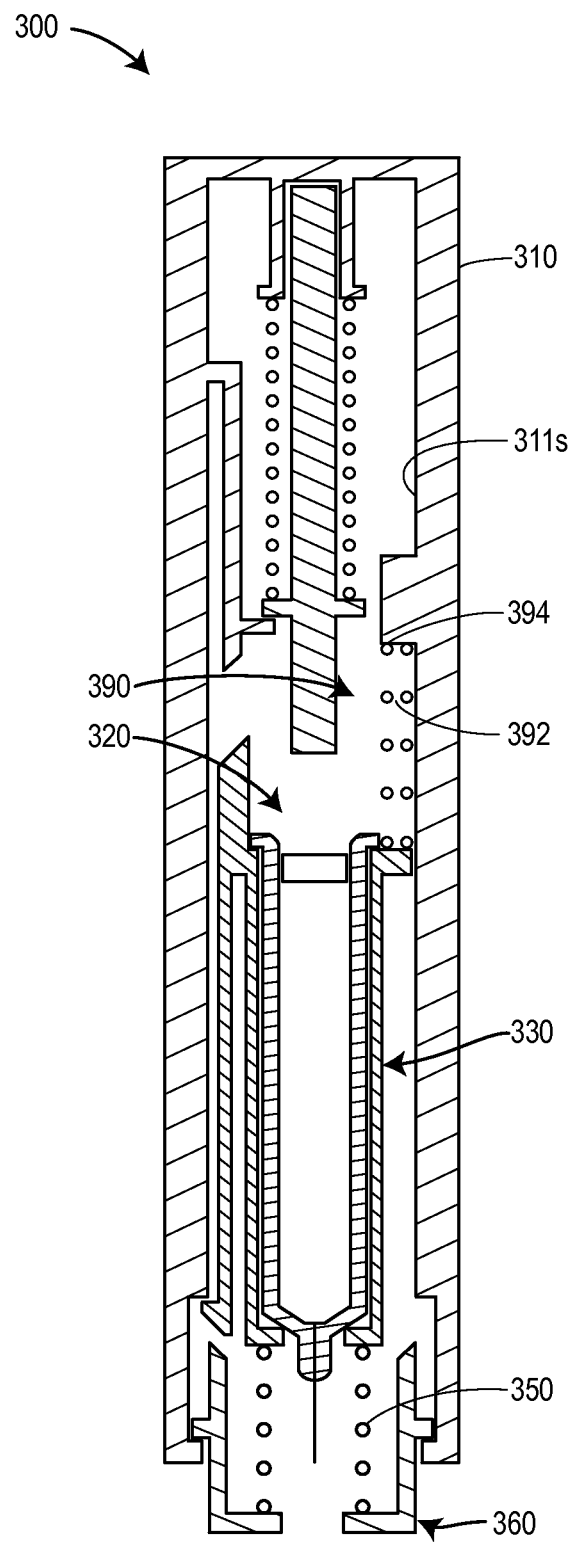
FIG. 5 is an elevational view in cross-section of a further embodiment of the injection device of the present disclosure.

FIG. 5 shows a further embodiment of the injection device 300 which comprises a locating mechanism 390 for defining the axial location of the drug storage device carrier 330, the drug storage device 320, and the guard 360. The locating mechanism 390 can comprise a biasing arrangement disposed between the drug storage device carrier 330 and the outer casing 310 which biases the drug storage device carrier 330. The biasing arrangement can comprise a container spring 392. The container spring 392 can be positioned on a ledge 394 or other suitable seating surface or element defined on the interior sidewall surface 311s of the outer casing 310. The locating mechanism 390 may be used in any of the previous embodiments of the injection device. The biasing arrangement of the locating mechanism 390 may have an energy or spring rate which is less than the energy of spring rate of the plunger loading mechanism 350.

Figure 6:
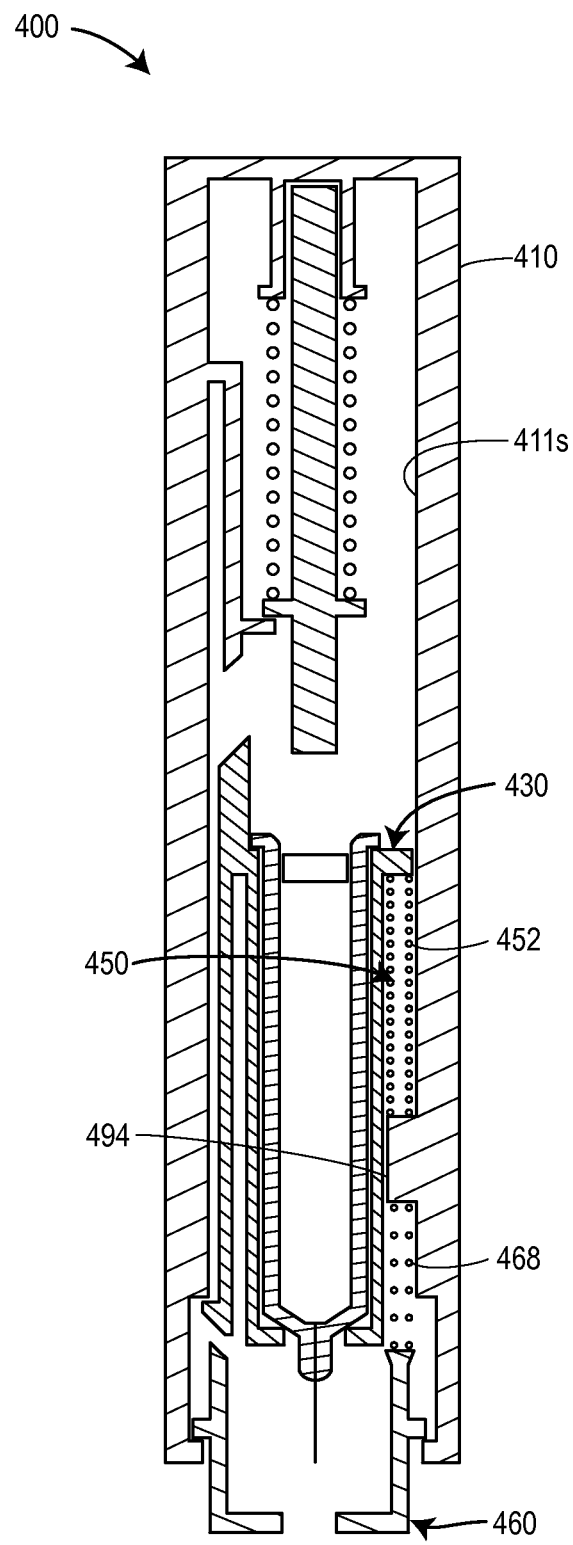
FIG. 6 is an elevational view in cross-section of still a further embodiment of the injection device of the present disclosure.

FIG. 6 shows a further embodiment of the injection device 400 comprising a plunger loading mechanism 450 which provides a force for moving the drug storage device carrier 430 proximally that is decoupled from the force used for biasing (activating) the guard 460, thereby improving the patient experience. As shown, the guard 460 may include a first biasing arrangement 468, which can be referred to as a needle guard biasing member, such as a spring, disposed between the guard 460 and the outer casing 410 to bias the guard 460. The needle guard biasing member 468 may be seated on a first surface of a ledge 494 or other suitable seating surface or element defined on the interior sidewall surface 411s of the outer casing 410. The plunger loading mechanism 450 may comprise a second biasing arrangement 452, such as a spring, disposed between the between the drug storage device carrier 430 and the outer casing 410 to bias the drug storage device carrier 430. The spring 452 may be seated on a second surface of the ledge 494 defined on the interior sidewall surface 411s of the outer casing 410. The needle guard biasing member 468 of the guard 460 and the second biasing arrangement 452 of the plunger loading mechanism 450 allow for two distinct forces: a first force to activate the guard 460 and a second force to move the drug storage device carrier 430 proximally to substantially reduce or eliminate the distance d between the stopper 426 of the drug storage device 420. The plunger loading mechanism 450 and guard 460/needle guard biasing member 468 can be implemented in any of the earlier described embodiments of the injection device.

Figure 7:
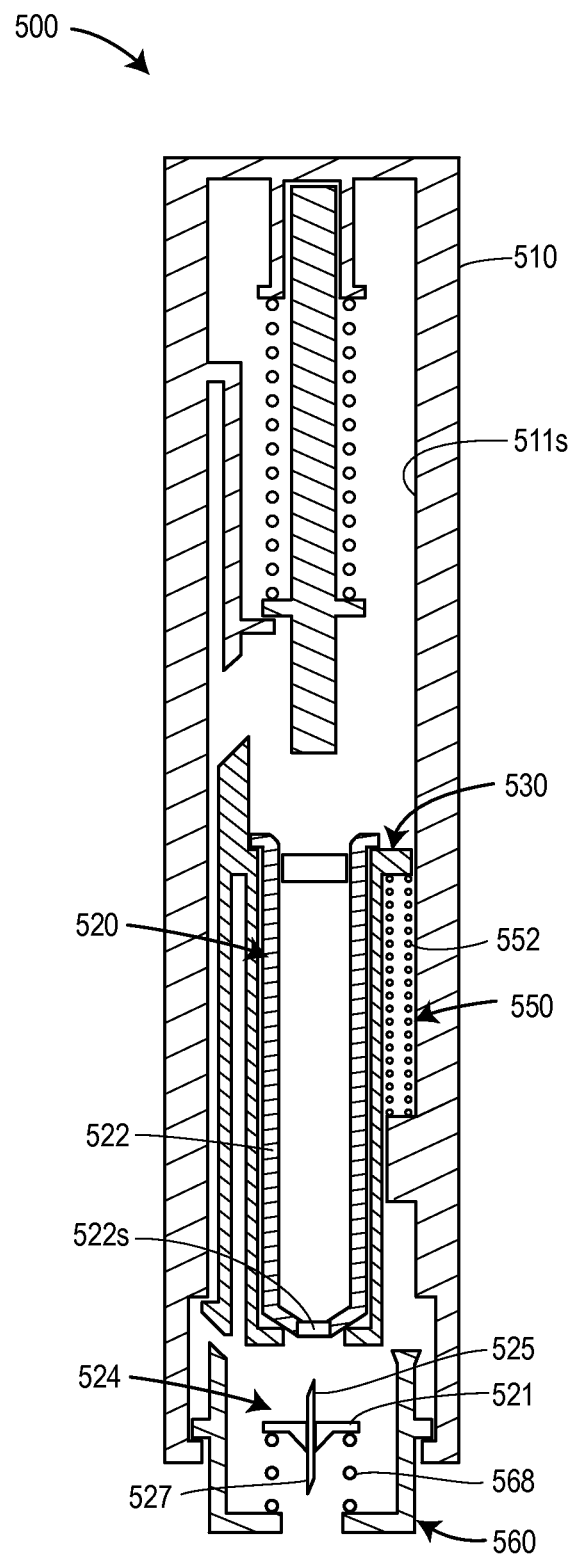
FIG. 7 is an elevational view in cross-section of another embodiment of the injection device of the present disclosure.

FIG. 7 shows a further embodiment of the injection device 500 for mini doser applications where the drug storage device 520 comprises a cartridge 522 having a distal end sealed by a septum 522s. As in the embodiment of FIG. 6, injection device 500 may comprise a plunger loading mechanism 550 including biasing arrangement 552, which provides a force for moving the drug storage device carrier 530 proximally that is decoupled from the force provided by biasing arrangement 568 used for biasing (activating) the guard 560, thereby improving the patient experience. In addition, the interior surface 511s of the outer casing 510 may include a mount 521 for fixedly positioning the dose delivery member 524 relative to the outer casing 510, such that the dose delivery member 524 is spaced from the drug storage device 520, prior to use of the device 500. The dose delivery member 524 may comprise a stake 525 extending proximally from the mount 521, and a needle 527 extending distally from the mount 521. The biasing arrangement 568 for the guard 460 may be disposed between the guard 560 and the mount 521 to bias the guard 560. Insertion of the needle 527 of the dose delivery member 524 into the patient's body tissue at the injection site takes place when the injection device 500 is pressed against the body tissue with enough force to overcome the biasing arrangement 568 and move the guard 560 into the outer casing 510. The stake 525 pierces the septum 522s of the cartridge 522 as the plunger rod 542, propelled by the high energy source 546, drives the drug storage device carrier 530 to its distal-most position, which causes the stake 525 of the dose delivery member 524 to pierce the septum 522s of the cartridge 522.

In still other embodiments of the injection device, the drug storage device and the drug storage device carrier may be configured as a single unitary component. For example, in one such embodiment the drug storage device carrier sleeve may be configured as a drug storage device primary container which includes a stopper, a dose delivery member and the elements of the carrier lock and the injection drive lock mechanisms described earlier.

The above description describes various systems and methods for use with a drug injection device. It should be clear that the system, drug injection device and/or methods can further comprise use of a medicament listed below with the caveat that the following list should neither be considered to be all inclusive nor limiting. The medicament will be contained in a reservoir. In some instances, the reservoir is the primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, NEUPOGEN® (filgrastim) and NEULASTA® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as EPOGEN® (epoetin alfa), ARANESP® (darbepoetin alfa), DYNEPO® (epoetin delta), MIRCERA® (methyoxy polyethylene glycol-epoetin beta), HEMATIDE®, MRK-2578, INS-22, RETACRIT® (epoetin zeta), NEORECORMON® (epoetin beta), SILAPO® (epoetin zeta), BINOCRIT® (epoetin alfa), epoetin alfa Hexal, ABSEAMED® (epoetin alfa), RATIOEPO® (epoetin theta), EPORATIO® (epoetin theta), BIOPOIN® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as VECTIBIX® (panitumumab), XGEVA™ (denosumab) and PROLIA™ (denosamab); other biological agents such as ENBREL® (etanercept, TNF-receptor/Fc fusion protein, TNF blocker), NEULASTA® (pegfilgrastim, pegylated filgastrim, pegylated G-CSF, pegylated hu-Met-G-CSF), NEUPOGEN® (filgrastim, G-CSF, hu-MetG-CSF), and NPLATE® (romiplostim); small molecule drugs such as SENSIPAR® (cinacalcet). The device may also be used with a therapeutic antibody, a polypeptide, a protein or other chemical, such as an iron, for example, ferumoxytol, iron dextrans, ferric glycolate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including ACTIVASE® (alteplase, tPA); ARANESP® (darbepoetin alfa); EPOGEN® (epoetin alfa, or erythropoietin); GLP-1, AVONEX® (interferon beta-1a); BEXXAR® (tositumomab, anti-CD22 monoclonal antibody); BETASERON® (interferon-beta); CAMPATH® (alemtuzumab, anti-CD52 monoclonal antibody); DYNEPO® (epoetin delta); VELCADE® (bortezomib); MLN0002 (anti-α4β7 mAb); MLN1202 (anti-CCR2 chemokine receptor mAb); ENBREL® (etanercept, TNF-receptor/Fc fusion protein, TNF blocker); EPREX® (epoetin alfa); ERBITUX® (cetuximab, anti-EGFR/HER1/c-ErbB-1); GENOTROPIN® (somatropin, Human Growth Hormone); HERCEPTIN® (trastuzumab, anti-HER2/neu (erbB2) receptor mAb); HUMATROPE® (somatropin, Human Growth Hormone); HUMIRA® (adalimumab); insulin in solution; INFERGEN® (interferon alfacon-1); NATRECOR® (nesiritide; recombinant human B-type natriuretic peptide (hBNP); KINERET® (anakinra); LEUKINE® (sargamostim, rhuGM-CSF); LYMPHOCIDE® (epratuzumab, anti-CD22 mAb); BENLYSTA™ (lymphostat B, belimumab, anti-BlyS mAb); METALYSE® (tenecteplase, t-PA analog); MIRCERA® (methoxy polyethylene glycol-epoetin beta); MYLOTARG® (gemtuzumab ozogamicin); RAPTIVA® (efalizumab); CIMZIA® (certolizumab pegol, CDP 870); SOLIRIS™ (eculizumab); pexelizumab (anti-C5 complement); NUMAX® (MEDI-524); LUCENTIS® (ranibizumab); PANOREX® (17-1A, edrecolomab); TRABIO® (lerdelimumab); TheraCim hR3 (nimotuzumab); Omnitarg (pertuzumab, 2C4); OSIDEM® (IDM-1); OVAREX® (B43.13); NUVION® (visilizumab); cantuzumab mertansine (huC242-DM1); NEORECORMON® (epoetin beta); NEUMEGA® (oprelvekin, human interleukin-11); NEULASTA® (pegylated filgastrim, pegylated G-CSF, pegylated hu-Met-G-CSF); NEUPOGEN® (filgrastim, G-CSF, hu-MetG-CSF); Orthoclone OKT3® (muromonab-CD3, anti-CD3 monoclonal antibody); PROCRIT® (epoetin alfa); REMICADE® (infliximab, anti-TNFα monoclonal antibody); REOPRO® (abciximab, anti-GP IIb/IIia receptor monoclonal antibody); ACTEMRA® (anti-IL6 Receptor mAb); AVASTIN® (bevacizumab), HuMax-CD4 (zanolimumab); RITUXAN® (rituximab, anti-CD20 mAb); TARCEVA® (erlotinib); ROFERON-A®-(interferon alfa-2a); SIMULECT® (basiliximab); PREXIGE® (lumiracoxib); SYNAGIS® (palivizumab); 146B7-CHO (anti-IL15 antibody, see U.S. Pat. No. 7,153, 507); TYSABRI® (natalizumab, anti-α4integrin mAb); VALORTIM® (MDX-1303, anti-B. anthracis protective antigen mAb); ABTHRAX™; VECTIBIX® (panitumumab); XOLAIR® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); ZENAPAX® (daclizumab); ZENAPAX® (daclizumab, anti-IL-2Rα mAb); ZEVALIN® (ibritumomab tiuxetan); ZETIA® (ezetimibe); ORENCIA® (atacicept, TACI-Ig); anti-CD80 monoclonal antibody (galiximab); anti-CD23 mAb (lumiliximab); BR2-Fc (huBR3/huFc fusion p rotein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1 mAb (MDX-1106 (ONO-4538)); anti-PDGFRα antibody (IMC-3G3); anti-TGβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, systems, methods, and elements thereof, have been described in terms of embodiments, they are not limited thereto. Rather, the appended claims should be construed broadly to include other variants and embodiments of same, which may be made by those skilled in the art without departing from the scope and range of equivalents of the device, systems, methods, and their elements.

What is claimed is:

1. A drug delivery device comprising:
   an outer casing including a tubular sidewall and a needle guard, the needle guard being movable relative to the tubular sidewall between an extended position and a retracted position;
   a primary container disposed in the outer casing and comprising a distal end carrying a dose delivery member, a proximal end, and an interior chamber extending between the distal and proximal ends, the interior chamber for storing a drug and a stopper movably disposed in the interior chamber for expelling the drug from the dose delivery member at the distal end;
   an injection drive mechanism comprising a plunger and a first energy source, the first energy source exerting a first force on the plunger such that upon activation of the injection drive mechanism the first energy source causes the plunger to urge the stopper toward the distal end of the primary container; and
   a plunger loading mechanism comprising a second energy source exerting a second force on the primary container to bias the primary container toward the injection drive mechanism, a magnitude of the second force being less than a magnitude of the first force, wherein the plunger loading mechanism is activated by moving the needle guard in an axial direction towards the injection drive mechanism, wherein upon activation of the plunger loading mechanism, the plunger loading mechanism urges and moves the primary container in an axial direction toward the injection drive mechanism to reduce a distance between the stopper and the plunger before the injection drive mechanism is activated;
   wherein continued urging by the plunger loading mechanism on the primary container causing movement of the primary container toward the injection drive mechanism activates the injection drive mechanism, thereby causing the first energy source to urge the stopper toward the distal end of the primary container.

2. The drug delivery device of claim 1, wherein the needle guard is disposed in proximity to the dose delivery member of the primary container.

3. The drug delivery device of claim 1, wherein the second energy source comprises a container biasing member disposed between and applying the second force to the outer casing and the primary container.

4. The drug delivery device of claim 3, wherein the container biasing member comprises a coil spring.

5. The drug delivery device of claim 3, wherein the container biasing member applies the second force to the needle guard and the primary container.

6. The drug delivery device of claim 1, wherein the first energy source comprises a coil spring, a gas pressure arrangement, or a gas releasing arrangement.

7. The drug delivery device of claim 1, wherein the dose delivery member comprises an injection needle.

8. The drug delivery device of claim 1, wherein the primary container comprises a syringe.

9. The drug delivery device of claim 1, further comprising a carrier lock for selectively locking the primary container and resisting the second force of the plunger loading mechanism when the device is in a ready-to-use mode, thereby limiting movement of the primary container relative to the injection drive mechanism.

10. The drug delivery device of claim 1, further comprising an injection drive lock for selectively locking the injection drive mechanism and resisting the first force when the device is in a ready-to-use mode, thereby limiting movement of the plunger relative to the primary container.

11. The drug delivery device of claim 1, further comprising a drug stored in the interior chamber of the primary container.

* * * * *